United States Patent [19]

Ross et al.

[11] Patent Number: 6,015,400
[45] Date of Patent: Jan. 18, 2000

[54] METHOD FOR PLACING A FEEDING TUBE

[75] Inventors: Jeffrey R. Ross, Dublin; Kathleen Rowland, Mason, both of Ohio

[73] Assignee: Abbott Laboratories, Abbott Park, Ill.

[21] Appl. No.: 09/003,177

[22] Filed: Jan. 5, 1998

[51] Int. Cl.[7] .................................................. A61M 31/00
[52] U.S. Cl. ......................... 604/506; 604/104; 604/117; 604/158; 604/161; 604/164; 604/264
[58] Field of Search .................................... 604/158, 161, 604/164, 264, 280, 104, 117, 536, 524, 506

[56] References Cited

U.S. PATENT DOCUMENTS

| | | |
|---|---|---|
| 4,762,519 | 8/1988 | Frimberger . |
| 5,037,387 | 8/1991 | Quinn et al. . |
| 5,098,378 | 3/1992 | Piontek et al. . |
| 5,112,310 | 5/1992 | Grobe . |
| 5,246,424 | 9/1993 | Wilk .......................................... 604/164 |
| 5,318,530 | 6/1994 | Nelson, Jr. . |
| 5,487,739 | 1/1996 | Aebischer et al. .................... 604/890.1 |
| 5,840,065 | 11/1998 | Goldhardt et al. ......................... 604/96 |

OTHER PUBLICATIONS

K. Sylvester et al., "Combined Laparoscopic–Endoscopic Gastrostomy", *Surgical Endoscopy*, 8:1072–1075 (1994).
Grathwohl et al., "Beside Videoscopic Placement of Feeding Tubes: Development of Fiberoptics Through the Tube", *Crit Care Med*, 25 (4): 629–634 (1997).

*Primary Examiner*—Wynn Wood Coggins
*Assistant Examiner*—Eric Kline
*Attorney, Agent, or Firm*—Brian R. Woodworth; Daniel J. Hulseberg

[57] ABSTRACT

A method for placing a feeding tube in a patient. The method includes the step of providing a needle defining a channel therethrough, the needle being constructed for insertion through an abdominal wall of a patient and having a distal end portion and a proximal end portion. The distal end portion of the needle is inserted through an abdominal wall of a patient. An endoscope constructed for insertion through the channel defined through the needle is provided and inserted through the channel defined through the needle. An external environment of the distal end portion of the needle is viewed using the endoscope in order to determine whether the distal end portion of the needle is positioned within a preselected portion of a gastrointestinal tract of a patient. A dilating device having a proximal end portion and a distal end portion is provided. The dilating device defines a channel therethrough. The dilating device is placed such that the needle is positioned within the channel defined through the dilating device. The dilating device is passed along the needle such that the distal end portion of said dilating device passes through an abdominal wall of a patient and into a preselected portion of a gastrointestinal tract of a patient. The needle is then removed from the patient. A feeding tube defining a channel therethrough is provided. The feeding tube has a proximal end portion and a distal end portion. The feeding tube is positioned such that the distal end portion of the feeding tube is positioned within the channel defined through the dilating device and the feeding tube is urged into a gastrointestinal tract of a patient. The dilating device is then removed from the patient.

13 Claims, 7 Drawing Sheets

METHOD FOR PLACING A FEEDING TUBE

TECHNICAL FIELD

This invention relates to an improved method for placing a feeding tube through a patient's abdominal wall and into a preselected section of a patient's gastrointestinal tract. In particular, the method of the present invention employs a percutaneous placement method with endoscopic position confirmation, the method being designed to reduce trauma to the patient and the time required for placement of the tube by eliminating the need to pass the feeding tube down the patient's esophagus.

BACKGROUND OF THE INVENTION

Gastrostomy and jejunostomy tubes are used to deliver nutritional products to the gastrointestinal tract of a patient having difficulty ingesting food. Gastrostomy tubes deliver the nutritional products percutaneously from an external source, through the patient's abdominal wall, and directly to the patient's stomach, while jejunostomy tubes deliver the nutritional products percutaneously into the patient's jejunum or small bowel. Gastrostomy and jejunostomy tubes are referred to collectively herein as "feeding tubes."

The first step in placing a feeding tube in a patient typically involves the passing of an endoscope down the patient's esophagus in order to view the esophagus and determine whether there are any obstructions or lesions in the esophagus that will inhibit or preclude passage of the feeding tube through the esophagus. The endoscope also is used to examine the interior of the stomach and/or the small bowel. Next, the doctor selects the site through which the feeding tube will be introduced and transilluminates the selected site by directing light outwardly from the endoscope such that the light shines through the patient's abdominal wall, thereby allowing the doctor to identify the entry site from a point outside of the patient's body. The doctor then makes an incision through the patient's abdominal wall into the stomach and passes a first end of a wire percutaneously into the stomach. The first end of the wire is grasped using a grasping tool associated with the endoscope, and the endoscope and the wire are drawn outwardly from the patient's stomach and esophagus through the patient's mouth. Upon completing this step of the procedure, a second end of the wire remains external to the patient's abdominal wall while the first end of the wire extends outwardly from the patient's mouth.

In one technique for feeding tube placement, the first end of the wire is attached to a first end of a feeding tube. By pulling on the second end of the wire, the feeding tube is pulled through the patient's mouth and esophagus, and into stomach. Further pulling of the second end of the wire causes the first end of the feeding tube to exit percutaneously from the stomach through the tract in the abdominal wall. The feeding tube is pulled outwardly through the tract until a retaining member mounted on the second end of the feeding tube engages the interior of the stomach. This technique is referred to as a "pull" technique.

In an alternative technique for feeding tube placement, a channel through the feeding tube is placed over the wire such that the feeding tube can be pushed along the length of the wire. As the feeding tube is pushed over the wire, it passes through the patient's mouth, esophagus, and stomach until the first end of the feeding tube exits through the incision in the abdominal wall. The feeding tube is then drawn outwardly through the abdominal tract until a retaining member on the second end of the feeding tube engages the interior of the stomach. The wire is then withdrawn from the patient through the feeding tube channel. This technique is referred to as a "push" technique.

Feeding tubes used with push and pull placement techniques define a feeding lumen therethrough. The feeding lumen is open to an external environment of the feeding tube at the second end of the tube, i.e., at the end of the tube proximal the retaining member. The first end of the feeding tubes placed using the pull technique is closed and preferably has a substantially conical shape in order to act as a dilator as the first end of the feeding tube is drawn through the incision. Thus, the feeding lumen of tubes placed using the pull technique is not open to an external environment of the feeding tube at the first end of the feeding tube.

Following placement of the feeding tube using either the push or the pull technique, the doctor typically inserts the endoscope again through the patient's mouth and esophagus in order to confirm the position and the orientation of the retaining member and feeding tube within the stomach.

In order to minimize the trauma to the patient associated with placement of the feeding tube, it is desirable to employ a feeding tube placement technique that reduces or eliminates the need to pass devices through the patient's esophagus, either into or from the stomach. As above-discussed, the push and pull techniques require at least five (5) separate one-way passes of devices through the esophagus, four (4) of which are attributable in whole or in part to scoping the patient prior to and following placement of the tube.

SUMMARY OF THE INVENTION

The present invention is directed to a method for percutaneously placing a feeding tube into the gastrointestinal tract of a patient. In accordance with the method of the present invention, a needle is provided and is inserted through the patient's abdominal wall into a preselected section of the patient's gastrointestinal tract. The needle defines a channel therethrough. An endoscope also is provided, the endoscope being configured for insertion through the channel defined through the needle. The endoscope is inserted into the channel defined through the needle and is used to confirm visually that the distal end of the needle is positioned properly within the preselected section of the patient's gastrointestinal tract. Upon confirmation that the distal end of the needle is properly positioned, the endoscope is withdrawn from the needle. A dilating device defining a lumen therethrough is provided and is positioned such that the needle is disposed within the lumen. The dilating device is inserted through the abdominal wall such that a distal end portion thereof enters the preselected section of the gastrointestinal tract of the patient as the dilating device is moved along the length of the needle. The needle is removed from the patient and a feeding tube defining a feeding lumen is provided. The feeding tube is inserted through the lumen defined by the dilating device and into the preselected section of the patient's gastrointestinal tract. The dilating device is then removed from the patient's abdominal wall.

In a second embodiment of the method of the present invention, a needle is provided and is inserted through the patient's abdominal wall into a preselected section of the patient's gastrointestinal tract. The needle defines a channel therethrough. An endoscope also is provided, the endoscope being configured for insertion through the channel defined through the needle. The endoscope is inserted into the channel defined through the needle and is used to confirm visually that the distal end of the needle is positioned properly within the preselected section of the patient's gastrointestinal tract. Upon confirmation that the distal end of the needle is properly positioned, the endoscope is withdrawn from the needle. A wire is provided and is placed through the channel defined through the needle such that a distal end of the wire is positioned within the preselected section of the patient's gastrointestinal tract. A feeding tube defining a feeding lumen is provided and is placed over the wire such that the wire is positioned within the feeding lumen. The feeding tube is urged along the length of the wire and through the patient's abdominal wall such that a distal end of the feeding tube is positioned within the preselected section of the patient's gastrointestinal tract. The wire is then removed from the feeding lumen defined through the feeding tube.

BRIEF DESCRIPTION OF THE DRAWINGS

In the accompanying drawings that form part of the specification, and in which like numerals are employed to designate like parts throughout the same.

DETAILED DESCRIPTION

While this invention is susceptible of embodiment in many different forms, this specification and the accompanying drawings disclose specific embodiments as examples of the invention. The invention is not intended to be limited to the embodiments so described. The scope of the invention is pointed out in and defined by the appended claims.

The figures illustrating the apparatus show some elements that are known and that will be recognized by one skilled in the art. The detailed descriptions of such elements are not necessary to an understanding of the invention, and accordingly, are herein presented only to the degree necessary to facilitate an understanding of the novel features of the present invention.

The present invention is practiced with certain conventional components the details of which, although not fully illustrated or described, will be apparent to those having skill in the art and an understanding of the necessary functions of such components.

The method of the invention will be described herein in the context of the accompanying figures which depict a method for placing a feeding tube percutaneously into the stomach of a patient. However, it will be appreciated by one of ordinary skill in the art that the method of the present invention can be employed for the purposes of placing feeding tubes into other preselected sections of the gastrointestinal tract of a patient, e.g., the small bowel. Accordingly, the detailed description set forth herein is intended to cover methods for placing feeding tubes into any preselected section of the gastrointestinal tract of a patient, including, but not limited to, the stomach and the small bowel.

Figure 1:
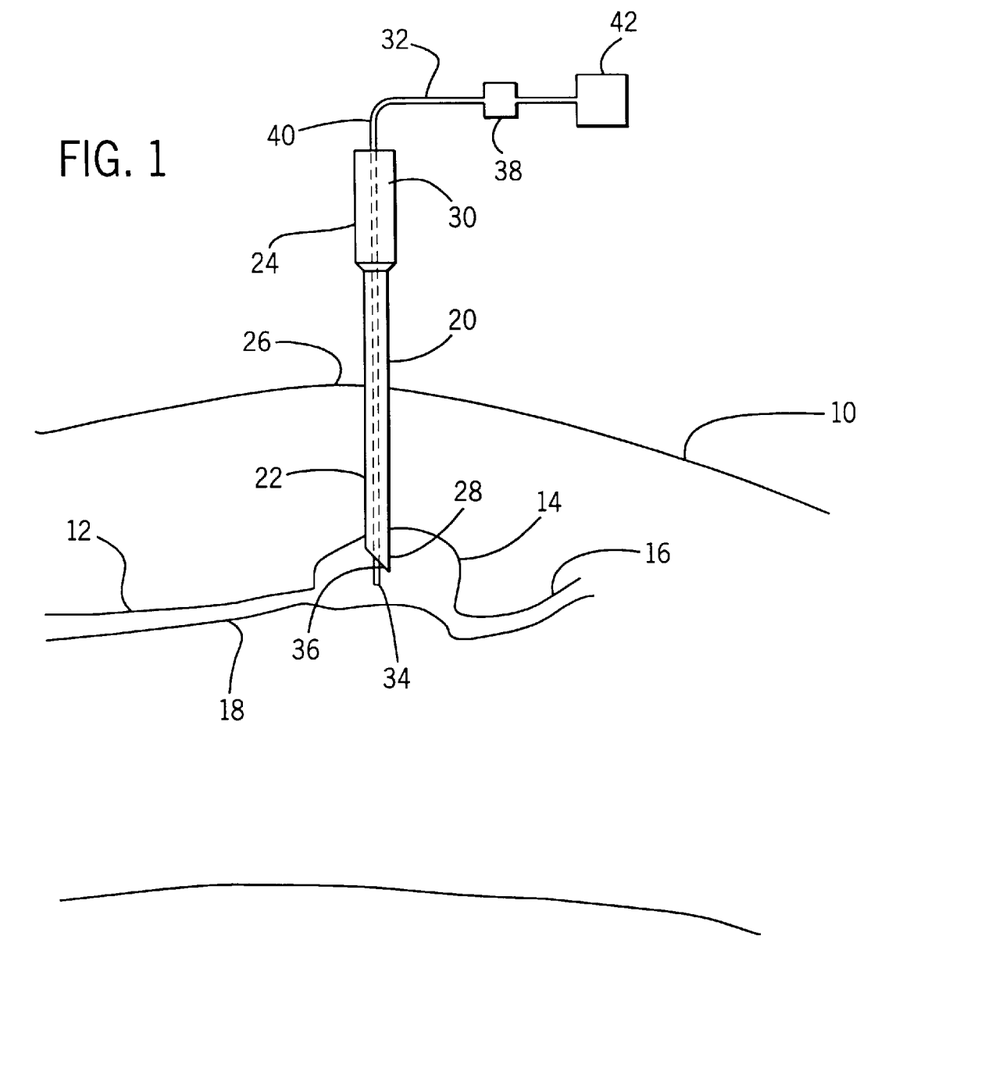
FIG. 1 is a plan view of a needle inserted percutaneously into a patient's gastrointestinal tract, the needle having an endoscope inserted therethrough in accordance with the method of the present invention.

A patient requiring a feeding tube is represented at 10 in FIG. 1. Patient 10 has an esophagus 12, a stomach 14, a small bowel 16, and gastrointestinal tract 18. It will be appreciated that gastrointestinal tract 18 includes, but is not limited to, esophagus 12, stomach 14, and small bowel 16. The location of stomach 14, small bowel 16, or any preselected portion of gastrointestinal tract 18 can be confirmed using known techniques. For example, the location of a selected portion of gastrointestinal tract 18 can be identified using ultrasound, fluoroscopy, or endoscopy.

The method of the present invention includes first and second embodiments. The first and second embodiments of the invention each include the same initial step of placing a needle 20 through abdominal wall 26 and into the preselected section of gastrointestinal tract 18. Accordingly, this portion of the method of the present invention will be described herein only once, although it is to be appreciated that this step is practiced in connection with both embodiments of the method of the present invention.

In accordance with the method of the present invention, needle 20 is provided. As depicted in FIG. 1, needle 20 has a distal end portion 22 and a proximal end portion 24. Distal end portion 22 preferably is constructed for insertion through abdominal wall 26 of patient 10 and into gastrointestinal tract 18. As depicted in FIG. 1, distal end portion 22 includes a beveled distal tip 28 which is configured for insertion through abdominal wall 26 and into gastrointestinal tract 18. Needle 20 can have a variety of sizes, configurations, and lengths. However, needle 20 preferably is constructed such that proximal end 24 thereof is external of patient 10 when distal tip 28 is positioned within gastrointestinal tract 18. Needle 20 can be constructed of a variety of known biocompatible materials, including, but not limited to, stainless steel. Needle 20 defines channel 30 therethrough along its length. Channel 30 provides fluid communication from proximal end portion 24 to distal end portion 22 through needle 20.

In accordance with the method of the present invention, distal end portion 22 of needle 20 is inserted through abdominal wall 26 of patient 10. A topical anesthetic can be used in order to numb the point of insertion of needle 20 into abdominal wall 26. Insertion of needle 20 is performed for the ultimate purpose of placing distal tip 28 of needle 20 within a preselected section of gastrointestinal tract 18. In the case of FIG. 1, the preselected section of gastrointestinal tract 18 is stomach 14. Needle 20 is inserted through abdominal wall 26 by applying an inwardly directed force to needle 20. As used herein, the term "inwardly" shall mean toward the patient while the term "outwardly" shall mean away from the patient.

Visual confirmation of the position of needle 20 during insertion thereof into gastrointestinal tract 18 is facilitated by forcing a small amount of a fluid through needle 20, thereby providing an "air space" or pocket between distal end portion 22 of needle 20 and the surrounding bodily tissues, including gastrointestinal tract 18. Upon visual confirmation of the location of the preselected portion of gastrointestinal tract 18, needle 20 can be urged into gastrointestinal tract 18. A method of this type is commonly used in connection with laparoscopic procedures in which a fluid, preferably carbon dioxide, is directed into the patient in order to create spaces between the patient's organs and tissues, thereby facilitating visualization and orientation during the laparoscopic procedure. This procedure is referred to as a pneumoperitoneum procedure. In laparoscopic surgery, this procedure is practiced with a veress needle. However, the method of the present invention is not intended to be limited to veress needles. Further, it will be appreciated that the amount of fluid necessary to provide an air space between distal end portion 22 of needle 20 and the surrounding bodily tissues in accordance with the method of the present invention will be less than that which is required during a laparoscopic procedure.

When properly inserted, needle 20 provides fluid contact between an external environment of patient 10 and the preselected section of gastrointestinal tract 18 through channel 30 defined through needle 20.

An endoscope 32 of known construction is provided as indicated in FIG. 1. Endoscope 32 includes optics 34 on distal end section 36 thereof. Optics 34 are electronically coupled to endoscope control unit 38 through cable section 40. Endoscope 32 is constructed to provide a visual image at display screen 42 of an external environment of distal end 36. In accordance with the present invention, endoscope 32 is configured such that it can be passed through channel 30 defined through needle 20, as depicted in FIG. 1.

In accordance with the method of the present invention, optics 34 and distal end portion 36 of endoscope 32 are passed through channel 30 defined through needle 20 after distal tip 28 of needle 20 has been positioned within the preselected section of gastrointestinal tract 18. As a result, optics 34 are positioned such that endoscope 32 can provide a visual image of the preselected section of gastrointestinal tract 18 at display screen 42.

In accordance with an alterative embodiment of the method of the present invention, optics 34 and distal end portion 36 of endoscope 32 are passed through channel 30 defined through needle 20 prior to the juncture at which distal tip 28 of needle is positioned within the preselected section of gastrointestinal tract 18, i.e., such that endoscope 32 and needle 20 are simultaneously inserted into gastrointestinal tract 18. Upon insertion of needle 20 through abdominal wall 26 and into the gastrointestinal tract 18, optics 34 will be positioned such that endoscope 32 can provide a visual image of the preselected section of gastrointestinal tract 18 at display screen 42.

In FIG. 1, optics 34 are positioned within stomach 14 in order to facilitate imaging by endoscope 32 of the external environment of distal end portion 22 of needle 20. That is, optics 34 and endoscope 32 provide a visual image of the preselected section of gastrointestinal tract 18. It will be appreciated optics 34 can be positioned within distal end portion 22 of needle 20 or can be substantially aligned with distal tip 28 of needle 20 and still provide a visual image of the preselected section of gastrointestinal tract 18 at display screen 42. The position of optics 34 relative to distal end 22 of needle 20 is unimportant to the method of the present invention so long as optics 34 provide a visual image of an external environment of the distal end portion 22 of needle 20. The positioning of optics 34 relative to distal tip 28 of needle 20 required to provide the desired image of the external environment of distal end portion 22 of needle 20 will be dependent upon a variety of factors including the optical characteristics of optics 34 and the size and other characteristics of channel 30 defined through needle 20.

Upon insertion of endoscope 32 and needle 20 through abdominal wall 26 of patient 10, an operator visually determines whether distal tip 28 of needle 20 is properly positioned within the preselected section of gastrointestinal tract 18. Visual determination is made by referring to display screen 42. The visual image provided by display screen 42 can be either a photographic representation of the external environment of distal end portion 22 of needle 20 or some other visual representation of such external environment, so long as an operator is able to determine the location of distal tip 28 of needle 20 by visual reference to display screen 42.

If it is visually determined that distal tip 28 of needle 20 is not properly positioned within gastrointestinal tract 18, needle 20 is repositioned prior to proceeding with the remaining steps of the method of the present invention. Repositioning of needle 20 can be performed with endoscope 32 within channel 30 defined through needle 20, or endoscope 32 can be withdrawn from channel 30 prior to repositioning. Repositioning may require the complete removal of needle 20 from patient 10, or may be achieved by manipulating needle 20 without removing it from patient 10. Subsequent to repositioning of needle 20, endoscope 32 is again used to provide a visual image at display screen 42 of the external environment of distal end portion 22 of needle 20.

If it is visually determined that distal tip 28 of needle 20 is properly positioned, endoscope 32 is withdrawn from abdominal wall 26 through needle 20. Withdrawal of endoscope 32 is achieved by applying an outwardly directed force to cable section 40. Endoscope 32 is then sterilized for future use or may be discarded.

Figure 2:
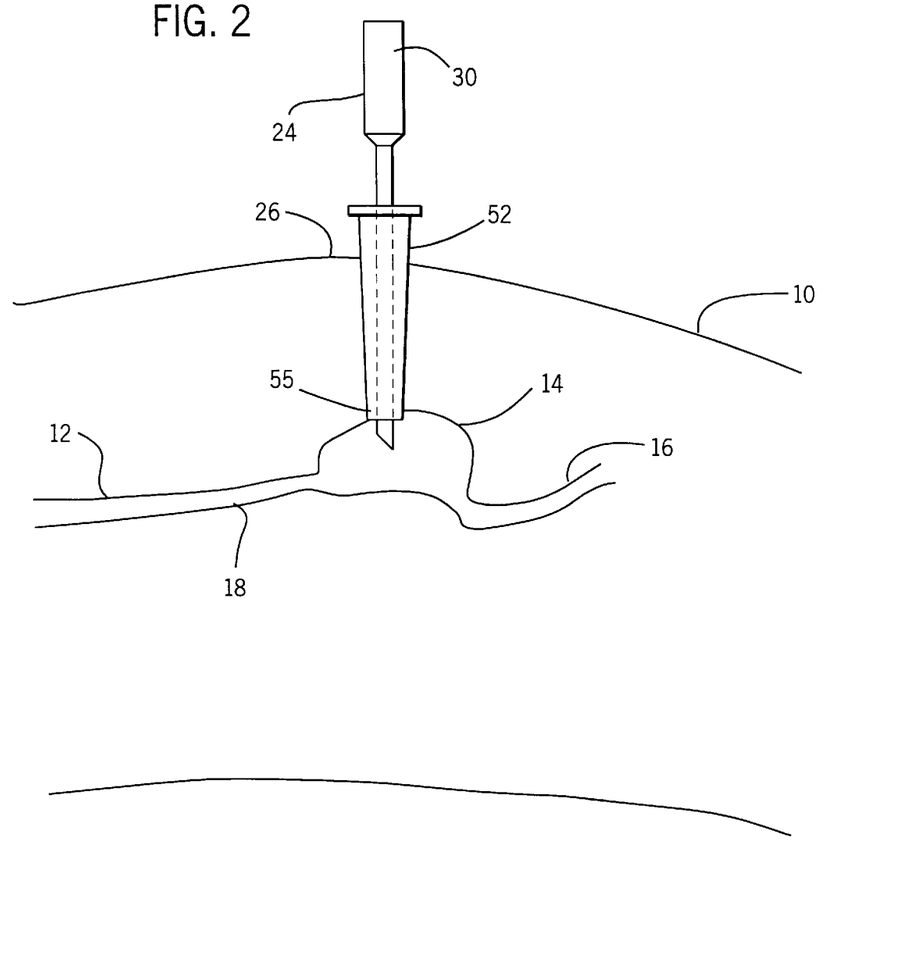
FIG. 2 is a plan view of a needle inserted percutaneously into a patient's gastrointestinal tract in accordance with the method of the present invention, the needle having a dilating device positioned about it.

In the first embodiment of the method of the present invention, a dilating device 52 is provided. Dilating device 52 can have a variety of known configurations. For example, dilating device 52 may comprise a single frustoconical member defining channel 54 therethrough, as depicted in the accompanying figures. Alternatively, dilating device 52 may comprise a plurality of frustoconical members of increasing diameter that can be placed sequentially over needle 20 in order to dilate the formed tract through abdominal wall 26. In another alternative embodiment, dilating device 52 can be constructed such that it is expandable, i.e., such that a radial dimension of dilating device 52 can be selectively increased or decreased, thereby allowing dilating device 52 to be used to increase the size of a tract formed through abdominal wall 26 and subsequently removed from abdominal wall 26.

Dilating device 52 is positioned such that it encircles needle 20, i.e., such that needle 20 is positioned within channel 54 defined by dilating device 52 as depicted in FIG. 2. After dilating device 52 is positioned about needle 20, dilating device 52 is urged inwardly along the length of needle 20 such that distal end portion 55 of dilating device 52 penetrates abdominal wall 26 and enters the preselected section of gastrointestinal tract 18. Proper placement of dilating device 52 through abdominal wall 26 and into gastrointestinal tract 18 can be confirmed using endoscope 32.

Upon positioning dilating device 52 through abdominal wall 26 and into gastrointestinal tract 18, needle 20, and endoscope 32 if it is still present, are withdrawn from abdominal wall 26 by applying an outwardly directed force thereto.

Figure 3:
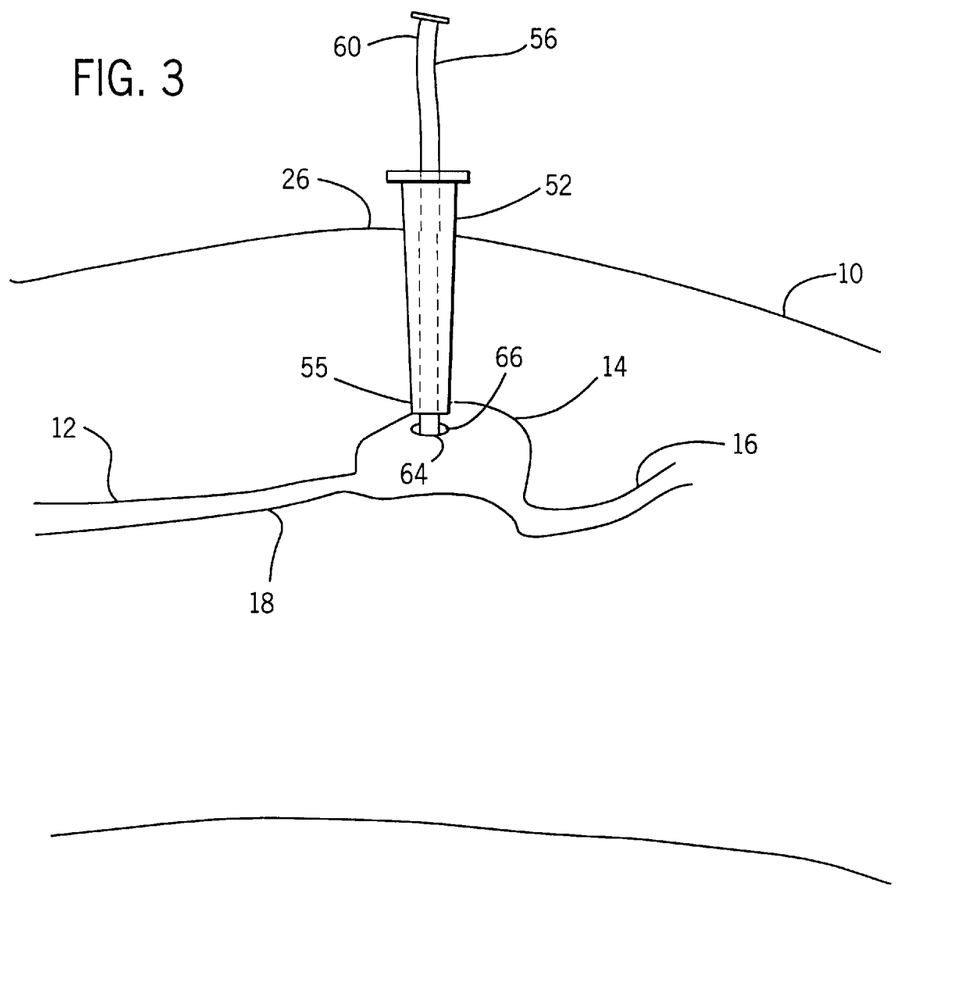
FIG. 3 is a plan view of a feeding tube inserted percutaneously into a patient's gastrointestinal tract, the feeding tube positioned within a dilating device in accordance with the method of the present invention.

Feeding tube 56 is then provided. Feeding tube 56 includes a distal end portion 58 and a proximal end portion 60. Feeding tube 56 channel 62 therethrough along its length. Channel 62 can be a feeding lumen of the feeding tube or can be a separate lumen defined along the length of feeding tube 56. Distal end portion 58 of feeding tube 56 is inserted into channel 54 defined through dilating device 52 and feeding tube 56 is urged inwardly through channel 54 such that distal end portion 58 thereof is positioned within the preselected section of gastrointestinal tract 18. Dilating device 52 is then removed from abdominal wall 26 by applying an outwardly directed force thereto.

Figure 6:
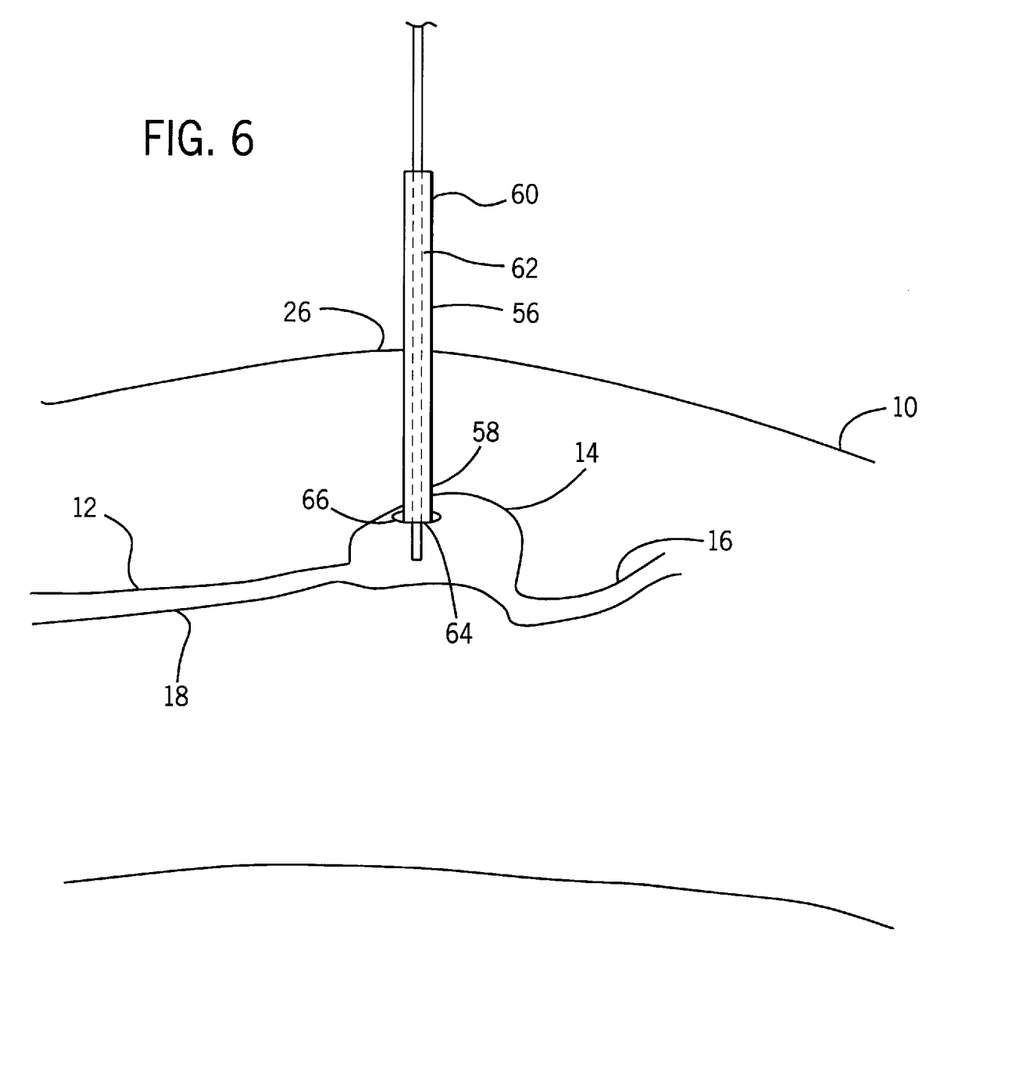
FIG. 6 is a plan view of a wire inserted percutaneously into a patient's gastrointestinal tract in accordance with a second embodiment of the method of the present invention, the wire having a feeding tube positioned about it.
Figure 7:
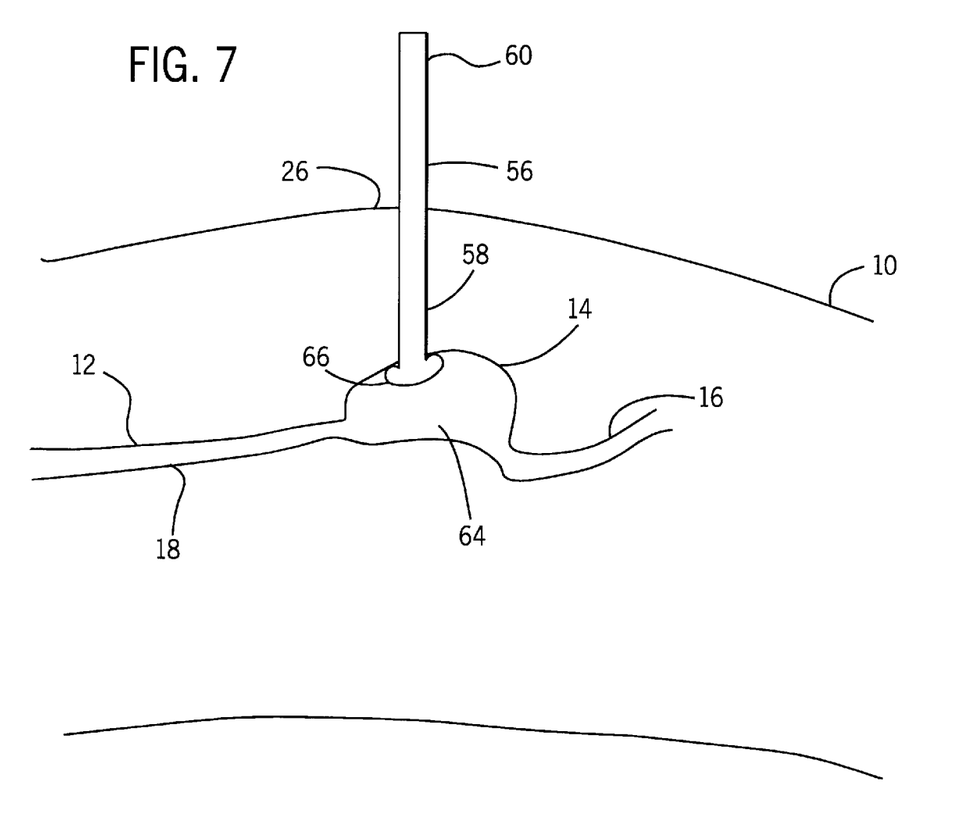
FIG. 7 is a plan view of a feeding tube positioned percutaneously into a patient's gastrointestinal tract.

Retaining member 66 is mounted on distal end portion 58 of feeding tube 56. Retaining member 66 is constructed such that it has an insertion configuration in which retaining member 66 has a dimension small enough that it can be inserted through abdominal wall 26 into gastrointestinal tract 18, as depicted in FIG. 6. Retaining member 66 also is constructed such that it has a retention configuration or position in which it engages a wall of gastrointestinal tract 18 when feeding tube 56 is urged outwardly relative to abdominal wall 26, thereby preventing the inadvertent removal of feeding tube 56 from patient 10, as depicted in FIG. 7.

Feeding tube 56 and retaining member 66 can have any of a variety of known configurations. For example, retaining member 66 can be an inflatable balloon member fluidly connected through an inflation lumen to an external environment of proximal end portion 60 of feeding tube 56, thereby permitting the balloon member to be inflated and deflated by an operator from a point external to patient 10. Retaining member 66 also can be mechanically operable between its insertion and retaining configurations.

In accordance with the first embodiment of the method of the present invention, retaining member 66 is caused to assume its retaining configuration after retaining member 66 has been positioned within the preselected section of gastrointestinal tract 18.

Figure 4:
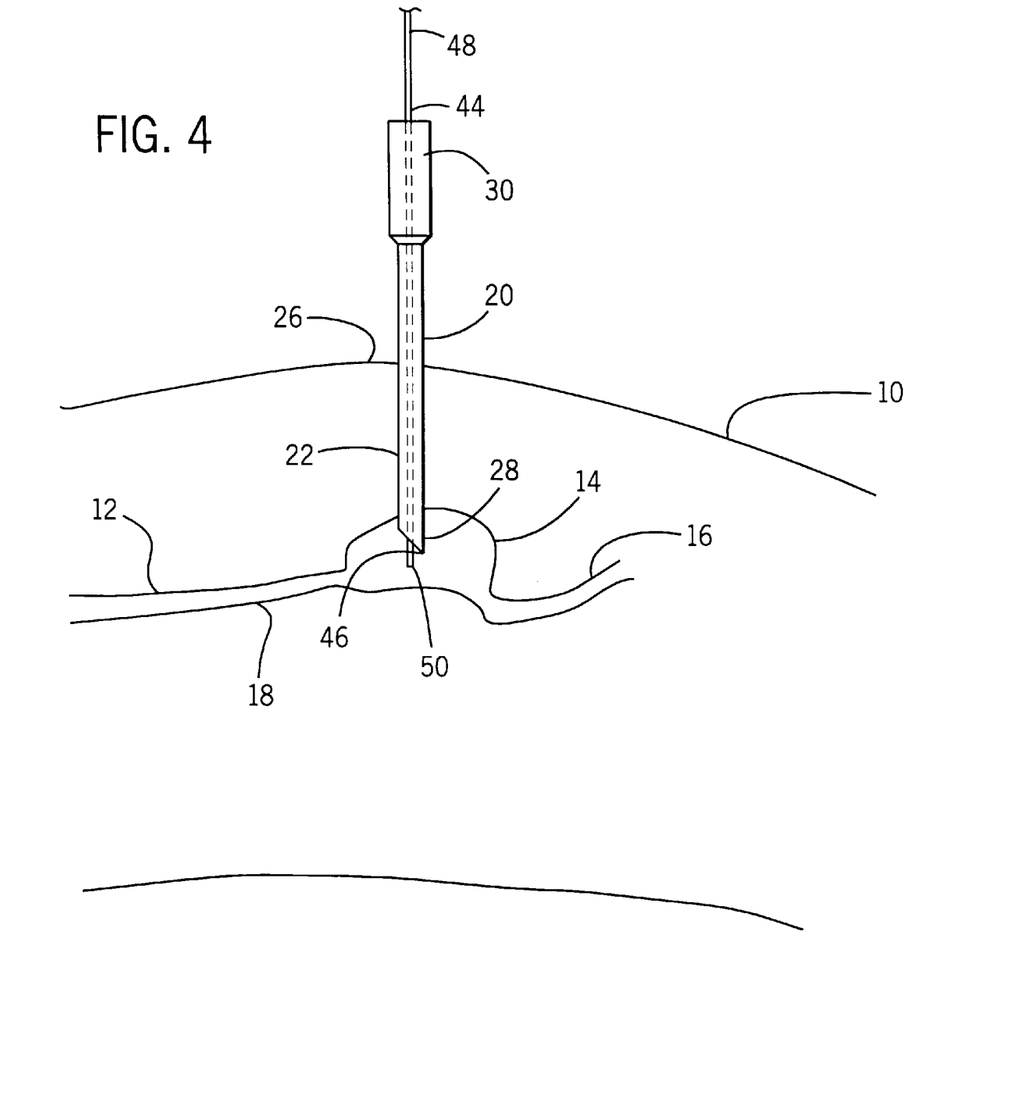
FIG. 4 is a plan view of a needle inserted percutaneously into a patient's gastrointestinal tract, the needle having a wire inserted therethrough in accordance with a second embodiment of the method of the present invention.

In the second embodiment of the method of the present invention, wire 44 is provided. Wire 44 is constructed such that it can be passed through channel 30 defined by needle 20. Wire 44 can be constructed of a variety of known biocompatible materials including metals and polymers. Wire 44 may include a single or multiple strands of such materials. Wire 44 includes a distal end portion 46 and a proximal end portion 48.

Distal tip 50 of wire 44 is inserted into channel 30 defined through needle 20 and is urged inwardly through needle 20 and into gastrointestinal tract 18, as depicted in FIG. 4. Proximal end portion 48 of wire 44 is positioned externally of needle 20 when distal tip 50 is positioned within gastrointestinal tract 18. Distal tip 50 of wire 44 can extend from distal tip 28 of needle 20 as depicted in FIG. 4 or distal tip 50 can be positioned within channel 30 defined through needle 20, so long as distal tip 50 is positioned within gastrointestinal tract 18.

After wire 44 has been properly positioned within gastrointestinal tract 18, needle 20 is withdrawn from abdominal wall 26 by applying an outwardly directed force thereto from proximal end portion 24. Withdrawal of needle 20 from abdominal wall 26 is performed such that distal tip 50 of wire 44 remains within gastrointestinal tract 18. Needle 20 is then discarded or sterilized for future use.

Figure 5:
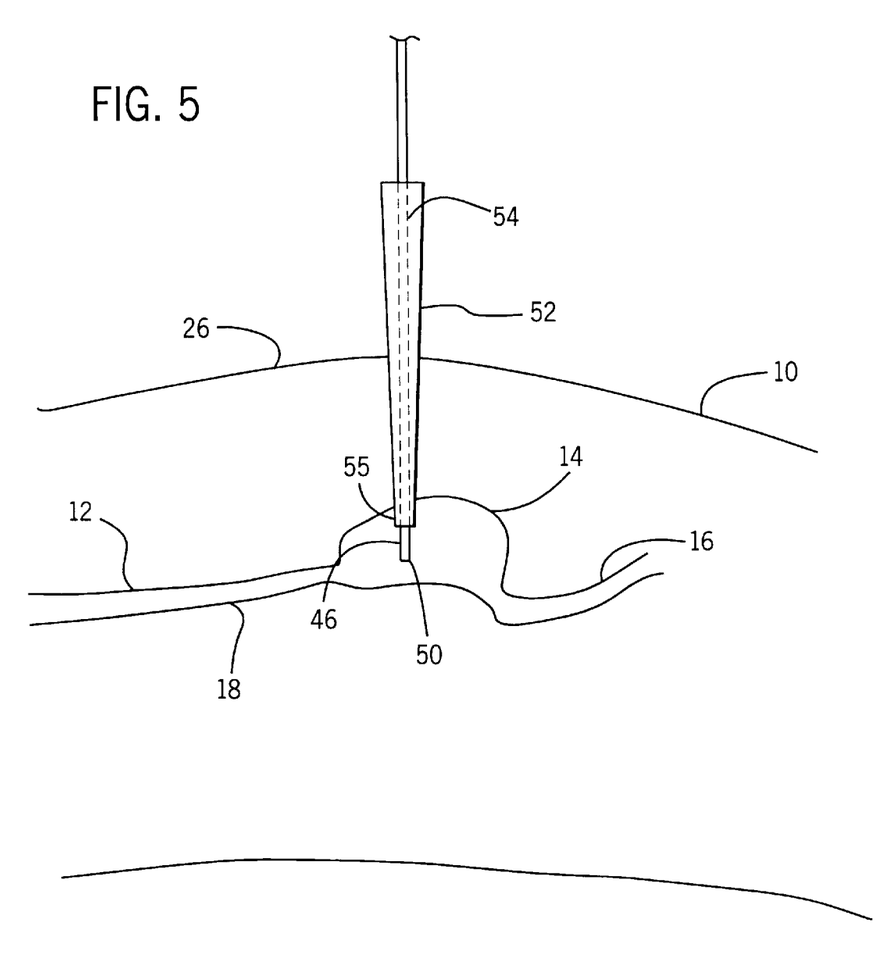
FIG. 5 is a plan view of a wire inserted percutaneously into a patient's gastrointestinal tract, the wire having a dilating device positioned about it in accordance with the second embodiment of the method of the present invention.

A dilating device 52 configured as above-discussed with respect to the first embodiment of the method of the present invention is provided, as depicted in FIG. 5. Dilating device 52 is placed over wire 44 such that wire 44 is positioned within dilator channel 54, as depicted in FIG. 5. Dilating device 52 is urged inwardly along wire 44 such that it passes through abdominal wall 26 and into gastrointestinal tract 18. Dilating device 52 is used to dilate the tract through abdominal wall 26 formed by needle 20.

Upon achieving the desired degree of dilation of the tract formed through abdominal wall 26, dilating device 52 is withdrawn from abdominal wall 26 and dilating device 52 is discarded or sterilized for future use.

Feeding tube 56 constructed in accordance with the above-discussed first embodiment of the present invention is provided. Feeding tube 56 is placed over proximal end portion 48 of wire 44 such that wire 44 is positioned within channel 62 and such that the distal end portion 58 of feeding tube 56 is directed toward abdominal wall 26. Feeding tube 56 is then urged toward abdominal wall 26 such that feeding tube 56 is advanced over wire 44 and through abdominal wall 26 until distal tip 64 of feeding tube 56 is positioned within gastrointestinal tract 18, as depicted in FIG. 4.

Upon placement of distal tip 64 of feeding tube 56 in gastrointestinal tract 18, wire 44 is withdrawn from channel 62 defined through feeding tube 54 by applying an outwardly directed force to proximal end portion 48 of wire 44. Wire 44 is then discarded or sterilized for future use.

In connection with the second embodiment of the present invention, dilating device 52 can be mounted on or formed integrally on distal end portion 58 of feeding tube 56 rather than being a separate structure, thereby enabling an operator simultaneously to dilate a tract through abdominal wall 26 and place feeding tube 56 therethrough. The separate steps of urging dilating device 52 and feeding tube 56 through abdominal wall 26 thereby are merged into a single step when dilating device 52 is mounted on or formed integrally on distal end portion 58 of feeding tube 56.

In certain cases it may not be necessary to use dilating device 52 prior to urging feeding tube 56 through abdominal wall 26. For example, needle 20 can be figured such that it provides an adequate tract through abdominal wall 26 whereby feeding tube 56 can be urged therethrough, thereby eliminating altogether the need to use dilating device 52.

In accordance with both the first and second embodiments of the method of the present invention, retaining member 66 is in its insertion configuration as feeding tube 56 is urged through abdominal wall 26, thereby minimizing the size of the tract required for insertion of feeding tube 56 through abdominal wall 26. Feeding tube 56 is urged into gastrointestinal tract 18 such that retaining member 66 is positioned entirely within gastrointestinal tract 18. When retaining member 66 and distal end portion 58 of feeding tube 56 are properly positioned, retaining member 66 is manipulated such that it assumes its retention configuration. As above-discussed, manipulation of retention member 66 can be performed by inflating a balloon with a fluid or by mechanically operating retention member 66.

Removal of feeding tube 56 from patient 10 is achieved by manipulating retaining member 66 such that it assumes its insertion configuration. Feeding tube 56 is then removed from patient 10 by exerting an outwardly directed force to proximal end portion 60 of feeding tube 56.

Although the present invention has been described herein in the context of certain embodiments, it will be appreciated that modifications thereto are possible. Such modifications are intended to be within the scope of the present invention, as defined by the appended claims.

What is claimed is:

1. A method for placing a feeding tube in a patient, the method comprising the steps of:

providing a needle, said needle defining a channel therethrough, said needle constructed for insertion through an abdominal wall of a patient, said needle having a distal end portion and a proximal end portion;

inserting said distal end portion of said needle through an abdominal wall of a patient;

providing an endoscope constructed for insertion into said channel defined through said needle;

inserting said endoscope into said channel defined through said needle;

viewing an external environment of said distal end portion of said needle using said endoscope in order to determine whether said distal end portion of said needle is positioned within a preselected portion of a gastrointestinal tract of a patient;

providing a dilating device having a proximal end portion and a distal end portion, said dilating device defining a channel therethrough;

positioning said dilating device such that said proximal end portion of said needle is positioned within said channel defined through said dilating device;

urging said dilating device along said needle such that said distal end portion of said dilating device passes through an abdominal wall of a patient and into a preselected portion of a gastrointestinal tract of a patient;

removing said needle and said endoscope from a patient;

providing a feeding tube defining a channel therethrough, said feeding tube having a proximal end portion and a distal end portion;

placing said distal end portion of said feeding tube in said channel defined through said dilating device;

urging said feeding tube into said channel defined through said dilating device such that said distal end portion of said feeding tube is urged into a gastrointestinal tract of a patient; and removing said dilating device from a patient.

2. A method for placing a feeding tube in a patient in accordance with claim 1, wherein said endoscope is inserted into said channel defined through said needle prior to inserting said distal end portion of said needle through an abdominal wall of a patient.

3. A method for placing a feeding tube in a patient in accordance with claim 1, wherein said endoscope is inserted into said channel defined through said needle after inserting said distal end portion of said needle through an abdominal wall of a patient.

4. A method for placing a feeding tube in a patient in accordance with claim 1, wherein said feeding tube includes a retaining member mounted on said distal end portion of said feeding tube.

5. A method for placing a feeding tube in a patient in accordance with claim 4, wherein said retaining member has an activated position for retaining said distal end portion of said feeding tube in a gastrointestinal tract of a patient, and wherein said retaining member has a retracted position for insertion through an abdominal wall of a patient.

6. A method for placing a feeding tube in a patient in accordance with claim 5, wherein said retaining member is in said retracted position when said feeding tube is urged through an abdominal wall of a patient, said method further comprising the step of causing said retaining member to assume said activated position after said distal end portion of said feeding tube is positioned within a gastrointestinal tract of a patient.

7. A method for placing a feeding tube in a patient, the method comprising the steps of:

providing a needle, said needle defining a channel therethrough, said needle constructed for insertion through an abdominal wall of a patient, said needle having a distal end portion and a proximal end portion;

inserting said distal end portion of said needle through an abdominal wall of a patient;

providing an endoscope constructed for insertion into said channel defined through said needle;

inserting said endoscope into said channel defined through said needle;

viewing an external environment of said distal end portion of said needle using said endoscope in order to confirm that said distal end portion of said needle is positioned within a preselected portion of a gastrointestinal tract of a patient;

withdrawing said endoscope from said channel defined through said needle;

providing a wire constructed for insertion into a gastrointestinal tract of a patient, said wire having a proximal end portion and a distal end portion;

inserting said distal end portion of said wire through said channel defined through said needle and into a gastrointestinal tract of a patient;

withdrawing said needle from an abdominal wall of a patient;

providing a dilating device having a proximal end portion and a distal end portion, said dilating device defining a channel therethrough;

positioning said dilating device such that said proximal end portion of said wire is positioned within said channel defined through said dilating device;

urging said dilating device along said wire such that said distal end portion of said dilating device passes through an abdominal wall of a patient and into a preselected portion of a gastrointestinal tract of a patient;

withdrawing said wire from an abdominal wall of a patient;

providing a feeding tube defining a channel therethrough, said feeding tube having a proximal end portion and a distal end portion;

placing said distal end portion of said feeding tube in said channel defined through said dilating device;

urging said feeding tube into said channel defined through said dilating device such that said distal end portion of said feeding tube is urged into a gastrointestinal tract of a patient; and removing said dilating device from an abdominal wall of a patient.

8. A method for placing a feeding tube in a patient in accordance with claim 7, wherein said endoscope is inserted into said channel defined through said needle prior to inserting said distal end portion of said needle through an abdominal wall of a patient.

9. A method for placing a feeding tube in a patient in accordance with claim 7, wherein said endoscope is inserted into said channel defined through said needle after inserting said distal end portion of said needle through an abdominal wall of a patient.

10. A method for placing a feeding tube in a patient in accordance with claim 7, wherein said feeding tube includes a retaining member mounted on said distal end portion of said feeding tube.

11. A method for placing a feeding tube in a patient in accordance with claim 10, wherein said retaining member has an activated position for retaining said distal end portion of said feeding tube in a gastrointestinal tract of a patient, and wherein said retaining member has a retracted position for insertion through an abdominal wall of a patient.

12. A method for placing a feeding tube in a patient in accordance with claim 11, wherein said retaining member is in said retracted position when the feeding tube is urged through an abdominal wall of a patient, said method further comprising the step of causing said retaining member to assume said activated position after said distal end portion of said feeding tube is positioned within a gastrointestinal tract of a patient.

13. A method for placing a feeding tube in a patient in accordance with claim 7, wherein the step of withdrawing said wire is performed after the step of urging said feeding tube.

\* \* \* \* \*